United States Patent
Adam et al.

[11] Patent Number: 5,091,382
[45] Date of Patent: Feb. 25, 1992

[54] CEPHALOSPORIN DERIVATIVES

[75] Inventors: Friedhelm Adam, Hofheim; Walter Dürckheimer, Hattersheim; Karl-Heinz Scheunemann, Frankfurt; Dieter Isert, Eschborn, Fed. Rep. of Germany; Gerhard Seibert, Darmstadt, all of Fed. Rep. of Germany

[73] Assignee: Hoechst Aktiengesellschaft, Frankfurt, Fed. Rep. of Germany

[21] Appl. No.: 552,058

[22] Filed: Jul. 13, 1990

[30] Foreign Application Priority Data

Jul. 15, 1989 [DE] Fed. Rep. of Germany ....... 3923541

[51] Int. Cl.$^5$ .................. C07D 501/36; A61K 31/545
[52] U.S. Cl. ..................................... 514/206; 540/227
[58] Field of Search ........................ 540/227; 514/206

[56] References Cited

U.S. PATENT DOCUMENTS 4,590,267 5/1986 Scheunemann et al. ........... 540/227
4,701,452 10/1987 Limbert et al. ..................... 540/227

Primary Examiner—Nicholas S. Rizzo
Attorney, Agent, or Firm—Finnegan, Henderson, Farabow, Garrett, and Dunner

[57] ABSTRACT

Cephalosporin derivatives of the general formula

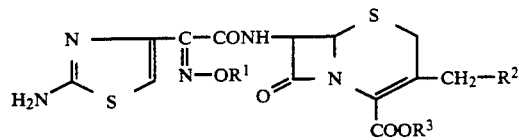

pharmaceutical preparations active against bacterial infections which contain such cephalosporin derivatives, processes for the preparation of the cephalosporin derivatives, use of the cephalosporin derivatives for the preparation of a pharmaceutical for combating bacterial infections, and starting products for the preparation of cephalosporin derivatives.

11 Claims, No Drawings

CEPHALOSPORIN DERIVATIVES

DESCRIPTION

The invention relates to novel cephalosporin derivatives and processes for their preparation, and in particular to cephem derivatives which are substituted in the 3'-position of the cephem ring by a 5-thio-1,3-thiazole ring hitherto not described in connection with cephalosporins and which have a very good antimicrobial activity against Gram-positive and Gram-negative bacteria and are therefore highly suitable as pharmaceuticals for the treatment of microbial infections. The invention furthermore relates to a process for their preparation, to pharmaceutical preparations containing them and to their preparation and use for combating bacterial infections.

The invention therefore relates to cephalosporin derivatives of the general formula I

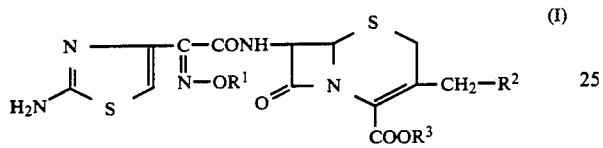

and their physiologically tolerable salts and acid addition salts, in which $R^1$ denotes hydrogen, optionally substituted $C_1$–$C_6$-alkyl, optionally substituted $C_2$–$C_6$-alkenyl, $C_2$–$C_6$-alkynyl, $C_3$–$C_7$-cycloalkyl, $C_4$–$C_7$-cycloalkenyl, the group

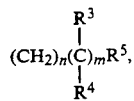

in which m or n in each case denote 0 or 1, $R^3$ and $R^4$ can be identical or different and denote hydrogen, aryl, a $C_1$–$C_4$-alkyl group or, together with the carbon atom to which they are bonded, form a methylene or a $C_3$–$C_7$-cycloalkylidene group; $R^5$ denotes a group —$CO_2R^6$ in which $R^6$ denotes hydrogen, $C_1$–$C_4$-alkyl or an equivalent of an alkali metal, alkaline earth metal, ammonium or an organic amine base;

$R^2$ stands for a 5-thio-1,3-thiazole radical of the formula II

in which $R^7$ has the meaning hydrogen, carboxyl, $C_1$–$C_4$-alkoxycarbonyl or carbamoyl, in which the amino group can optionally also be monosubstituted or disubstituted by $C_1$–$C_4$-alkyl, or two of the alkyl groups on the nitrogen can be closed to give a dimethylene to pentamethylene ring and $R^3$ denotes hydrogen, a physiologically tolerable cation or an easily cleavable ester group and in which the $R^1O$ group is in the syn position.

The present invention is preferably directed to compounds in which $R^1$, $R^7$ and $R^3$ have the following meanings:

$R^1$ = hydrogen $C_1$–$C_4$-alkyl, such as, for example, methyl, ethyl, propyl, isopropyl, butyl, in particular methyl and ethyl, preferably methyl, $C_1$–$C_4$-alkyl which is monosubstituted or polysubstituted, in particular monosubstituted to trisubstituted by halogen, such as, for example, chlorine or fluorine, in particular fluorine by $C_1$–$C_6$-, preferably $C_1$–$C_4$-alkylthio, such as, for example, methylthio, ethylthio, propylthio, butylthio, in particular methylthio and ethylthio, by $C_1$–$C_6$-, preferably $C_1$–$C_4$-alkyloxy, such as, for example, methoxy, ethoxy, propoxy, isopropoxy and butoxy, in particular methoxy and ethoxy, by aryl, in particular phenyl or by heteroaryl, such as, for example, pyridyl, furyl, $C_2$–$C_6$-, preferably $C_2$–$C_4$-alkenyl, such as, for example, vinyl or allyl, in particular allyl, which can also be monosubstituted or polysubstituted, in particular monosubstituted, by halogen, such as, for example, chlorine and bromine, in particular by chlorine, $C_2$–$C_3$-alkynyl, such as, for example, ethynyl or propargyl in particular propargyl, $C_3$–$C_7$-, preferably $C_3$–$C_5$-cycloalkyl, such as, for example, cyclopropyl, cyclobutyl and cyclopentyl, in particular cyclobutyl and cyclopentyl, $C_4$–$C_7$-, preferably $C_5$–$C_6$-cycloalkenyl, such as, for example, cyclopentyl and cyclohexyl, in particular cyclopentenyl, or the group

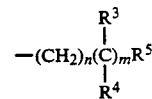

in which m and n in each case denote 0 or 1 and preferably where either m or n stand for 0, $R^3$ and $R^4$, which can be identical or different, have the meaning hydrogen, aryl, in particular phenyl, $C_1$–$C_4$-alkyl, such as, for example, methyl, ethyl, propyl, butyl, in particular methyl, or in which $R^3$ and $R^4$, together with the carbon atom to which they are bonded, form a methylene or a $C_3$–$C_7$-, preferably $C_3$–$C_5$-cycloalkylidene group, such as, for example, cyclopropylidene, cyclobutylidene or cyclopentylidene, in particular cyclopropylidene, $R^5$ stands for a group —$COOR^6$, in which $R^6$ can be hydrogen, $C_1$–$C_4$-alkyl, such as, for example, methyl, ethyl, propyl, isopropyl, butyl, isobutyl and tert.-butyl, in particular tert.-butyl, or an equivalent of an alkali metal, preferably sodium and potassium, an alkaline earth metal, such as, for example, calcium and magnesium, in particular calcium, or ammonium or an organic amine base, such as, for example, diisopropylamine, dicyclohexylamine and triethylamine, in particular triethylamine.

Very particularly preferred for $R^1$ are hydrogen or $C_1$–$C_4$-alkyl, in particular methyl and carboxymethyl.

$R^7$ preferably has the meaning hydrogen, carboxyl, $C_1$-$C_4$-alkoxycarbonyl, such as, for example, methoxy-, ethoxy-, propoxy-, isopropoxy-, butoxy-, sec.-butoxy-or tert.-butoxycarbonyl, in particular methoxy-, ethoxy- or tert.-butoxycarbonyl, carbamoyl, carbamoyl which is monosubstituted or disubstituted on the nitrogen by $C_1$-$C_4$-alkyl, such as, for example, methyl, ethyl, propyl, isopropyl or butyl, preferably methyl or in which two of the alkyl groups on the nitrogen can also be closed to give a di- to pentamethylene ring, preferably a tetra- or pentamethylene ring, in particular to give a tetramethylene ring.

Very particularly preferred for $R^7$ are hydrogen, carboxyl, $C_1$-$C_4$-alkoxycarbonyl, in particular methoxycarbonyl, carbamoyl and pyrrolidinocarbonyl.

$R^3$ preferably stands for hydrogen, a physiologically tolerable cation or one of the easily cleavable ester groups which is described precisely below. A particularly preferred group are the lower alkanoyloxyalkyl esters, such as, for example, the 2,2-dimethylpropionyloxymethyl ester. Possible physiologically tolerable cations are alkali metal cations, preferably sodium or potassium; alkaline earth metal cations, preferably magnesium and calcium; ammonium and organic amine bases, such as, for example, diisopropylamine, dicyclohexylamine and triethylamine, in particular triethylamine.

The invention furthermore relates to a process for the preparation of compounds of the general formula I and their physiologically tolerable salts and acid addition salts, which comprises a) reacting a compound of the general formula III

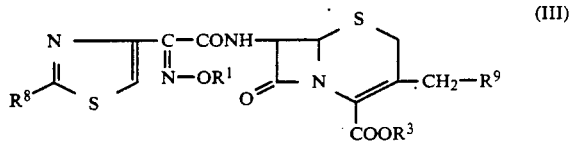

or its salts, in which $R^1$ and $R^3$ have the above-mentioned meaning, $R^8$ denotes an amino or a protected amino group and $R^9$ denotes a group exchangeable with 5-thio-1,3-thiazole or 5-thio-1,3-thiazole substituted in position 4, which correspond to the radical $R^2$ in the formula (I), with such a 5-mercapto-1,3-thiazole or one of its 4-substituted derivatives, cleaving off a protective group which may be present and, if necessary, converting the product obtained into a physiologically tolerable salt or acid addition salt, or b) reacting a 7-amino-cephem compound of the general formula IV

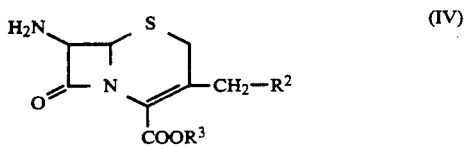

or its salts or acid addition salts, in which $R^2$ and $R^3$ have the abovementioned meaning and in which the amino group can also be present in the form of a reactive derivative, with a thiazol-4-yl-2-synoximeacetic acid of the general formula V

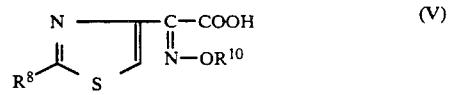

in which $R^8$ has the above meaning and $R^{10}$ has the meaning $R^1$, where in the case in which $R^1$ in formula (I) is hydrogen, $R^{10}$ denotes a protective group, or with an activated derivative of this compound, cleaving off a protective group which may be present and, if necessary, converting the product obtained into a physiologically tolerable salt or acid addition salt.

If $R^3$ stands for an easily cleavable ester group, $R^3$ can have the meaning of radicals customary in penicillin and cephalosporin chemistry, such as, for example, lower alkyl esters, such as, for example, methyl, ethyl, propyl, isopropyl, butyl, isobutyl, tert.-butyl, pentyl, tert.-pentyl and hexyl esters, lower alkenyl esters, such as, for example, vinyl or allyl esters; lower alkynyl esters, such as, for example, propargyl esters; lower alkoxyalkyl esters, such as, for example, methoxymethyl, ethoxymethyl, isopropoxymethyl, 1-methoxyethyl or 1-ethoxyethyl esters; lower alkylthioalkyl esters, such as, for example, methylthiomethyl, ethylthiomethyl, ethylthioethyl or isopropylthiomethyl esters; lower alkyl esters substituted by amino and carboxyl, such as, for example, 2-amino-2-carboxyethyl esters or 3-amino-2-carboxypropyl esters; by lower alkyl esters substituted by protected amino and protected carboxyl, such as also by lower alkoxycarbonylamino and mono-, di- or triphenylalkoxycarbonyl-substituted lower alkyl esters, such as, for example, 2-tert.-butoxycarbonylamino-2-benzhydryloxycarbonylethyl or 3-tert.-butoxycarbonylamino-3-benzhydryloxycarbonylpropyl ester; lower mono-, di- or trihalogenoalkyl esters, such as, for example, 2-iodoethyl or 2,2,2-trichloroethyl ester; lower alkanoyloxyalkyl esters, such as, for example, acetoxymethyl, propionyloxymethyl, butyryloxymethyl, isobutyryloxymethyl, valeryloxymethyl, pivaloyloxymethyl, hexanoyloxymethyl, 2-acetoxymethyl, 2-propionyloxyethyl, butyryloxyethyl, isobutyryloxyethyl, valeryloxy-ethyl, pivaloyloxyethyl or hexanoyloxyethyl esters; lower alkoxycarbonyloxyalkyl esters, such as, for example, methoxycarbonyloxyethyl, ethoxycarbonyloxyethyl, propoxycarbonyloxyethyl or isopropoxycarbonyloxyethyl esters; cycloalkoxycarbonyloxyethyl esters, such as, for example, cyclopentyloxycarbonyloxyethyl or cyclohexyloxycarbonyloxyethyl esters; lower alkylsulfonyl esters, such as, for example, mesylmethyl or 2-mesylethyl esters; lower mono-, di- or triphenylalkyl esters which can carry one or more substituents, such as, for example, benzyl, 4-nitrobenzyl, phenethyl, benzhydryl, trityl, bis(methoxyphenyl)methyl, 3,4-dimethoxybenzyl or 4-hydroxy-3,5-di-tert.-butylbenzyl esters; aryl esters which can carry one or more substituents, such as, for example, phenyl, tolyl, tert.-butylphenyl, xylyl, mesityl, cumenyl or salicyl esters; or heterocyclic esters, such as, for example, phthalidyl esters.

The term "lower" occurring in the definition of $R^3$ denotes $C_1$-$C_6$ for saturated radicals, preferably $C_1$-$C_4$-carbon atoms and $C_2$-$C_6$ for unsaturated radicals, preferably $C_2$-$C_4$-carbon atoms.

If the preparation of the compounds of the general formula (I) is intended to take place by nucleophilic exchange of $R^9$ in the compounds of the general formula (III) with 5-mercapto-1,3-thiazole or one of its indicated derivatives, possible radicals $R^9$ are in particular acyloxy radicals of lower aliphatic carboxylic acids, preferably having 1 to 4 carbon atoms, such as, for example, acetoxy or propionyloxy, in particular acetoxy, which can optionally be substituted, such as, for example, chloroacetoxy or acetylacetoxy. Other groups are also possible for $R^9$, such as, for example, halogen, in particular chlorine, bromine or iodine, or carbamoyloxy.

Starting compounds of the general formula (III), in which $R^9$ stands for acetoxy, or their salts, such as, for example, the sodium or potassium salt are preferably employed in the nucleophilic exchange reaction. When using compounds of the general formula (IV), these can likewise be obtained by nucleophilic exchange in a manner known per se, for example from the 7-aminocephalosporanic acid or from the 7-aminocephalosporanic acid protected on the amino group. The nucleophilic exchange reaction is carried out in a solvent, preferably in water or in a mixture of water and an organic solvent easily miscible with water, such as, for example, acetone, dioxane, acetonitrile, dimethylformamide, dimethyl sulfoxide or ethanol. The reaction temperature is in general in the range from about 10° to 100° C., preferably between 20° and 80° C. The base component is added in amounts which are approximately between equimolar amounts and an excess of up to 15-fold. The reaction is advantageously carried out in the vicinity of the neutral point, preferably at a pH in the range from about 5 to about 8, for example in the form of the sodium salt of 5-mercapto-1,3-thiazole or one of its derivatives.

If the group $R^8$ is present as the protected amino function, the protective groups known in peptide chemistry, for example tert.-butyl, tert.-amyl, benzyl, p-methoxybenzyl, trityl or benzhydryl, preferably trityl; such as, for example, trimethylsilyl; optionally substituted aliphatic acyl, such as, for example, formyl, chloroacetyl, bromoacetyl, trichloroacetyl and trifluoroacetyl, preferably formyl; or optionally substituted alkoxycarbonyl such as, for example, trichloroethoxycarbonyl, benzyloxycarbonyl or tert.-butyloxycarbonyl, preferably tert.-butyloxycarbonyl and benzyloxycarbonyl or dimethylaminomethylene, are suitable as amino-protective groups.

If $R^1$ in the general formula I has the meaning hydrogen, $R^{10}$ in the general formula (V) stands for an easily cleavable group known from peptide and cephalosporin chemistry, preferably for benzhydryl, trityl, tetrahydropyranyl or 1-methoxy-1-methylethyl. Trityl and 1-methoxy-1-methylethyl are particularly preferred for $R^{10}$.

The protective groups can be cleaved in a manner known per se after the exchange reaction, for example the trityl and 1-methoxy-1-methylethyl group can be cleaved by means of acid, such as, for example, acetic acid, trifluoroacetic acid or formic acid, or the benzyloxycarbonyl group can be cleaved hydrogenolytically.

The reaction products of the formula (I) can be isolated from the reaction mixture in a customary manner, for example by freeze-drying in the aqueous phase, by chromatography or even by precipitating at pH 3–4.

The acylation of the compounds of the general formula (IV) or their acid addition salts, for example using hydrochloric acid, hydrobromic acid or maleic acid, is carried out with a carboxylic acid of the general formula (V) or with a reactive derivative of such a carboxylic acid. In some cases here, it is advantageous to protect the 2-amino group and the oxime group in the compounds of the general formula (V) before the reaction. The protective groups described above for $R^8$ and $R^{10}$ are suitable as amino-protective groups. The protective group can be cleaved off after the acylation in a manner known per se, for example the trityl group and 1-methoxy-1-methylethyl group can be cleaved off by means of a carboxylic acid, such as, for example, formic acid or trifluoroacetic acid, or the chloroacetyl group can be cleaved off by means of thiourea. If the carboxylic acids of the general formula V and their derivatives protected on the amino and oxime group are employed themselves as acylating agents, the reaction is expediently carried out in the presence of a condensing agent, for example a carbodiimide, such as, for example, N,N'-dicyclohexylcarbodiimide.

The activation of the carboxylic acids of the general formula (V) can be carried out in a particularly favorable manner by treatment with certain carboxamides and, for example, phosgene, phosphorus pentachloride, tosyl chloride, thionyl chloride or oxalyl chloride, such as is described in German Patent No. 2,804,040.

Activated derivatives of carboxylic acids of the general formula (V) which are suitable are in particular also halides, preferably chlorides, which are obtained in a manner known per se by treatment with halogenating agents, such as, for example, phosphorus pentachloride, phosgene or thionyl chloride under mild reaction conditions known from the literature for cephalosporin chemistry.

Activated derivatives of the carboxylic acids of the general formula (V) which are suitable are in addition the anhydrides and mixed anhydrides, azides and activated esters, preferably with p-nitrophenol, 2,4-dinitrophenol, methylcyanohydrin, N-hydroxysuccinimide and N-hydroxyphthalimide, in particular those with 1-hydroxybenzotriazole and 6-chloro-1-hydroxybenzotriazole. Mixed anhydrides which are particularly suitable are those with lower alkanoic acids, such as, for example, acetic acid, and particularly preferably those with substituted acetic acids, such as, for example, trichloroacetic acid, pivalic acid or cyanoacetic acid. However, the mixed anhydrides of sulfonic acids, such as, for example, benzenesulfonic acid, toluenesulfonic acid or ethylbenzenesulfonic acid, or carbonic acid half esters, which are obtained, for example, by reaction of the carboxylic acids of the formula (V), in which the amino group is protected, with benzyl, p-nitrobenzyl, isobutyl, ethyl or allyl chloroformates, are particularly suitable. The activated derivatives can be reacted as isolated substances, but also in situ.

In general, the reaction of the cephem derivatives of the general formula (IV) is carried out using a carboxylic acid of the general formula (V) or an activated derivative of this in the presence of an inert solvent. Chlorinated hydrocarbons, preferably such as methylene chloride and chloroform; ethers, such as, for example, diethyl ether, preferably tetrahydrofuran and dioxane; ketones, preferably such as acetone and butanone; amides, preferably such as dimethylformamide and dimethylacetamide, or pyridine are particularly suitable. However, it may also prove advantageous to use mixtures of the solvents mentioned. This is often the case when the cephem compound of the general formula (IV) is reacted with an activated derivative of a carboxylic acid of the formula (V) generated in situ.

The reaction of cephem compounds of the formula (IV) with carboxylic acids of the formula (V) or their activated derivatives can be carried out in a temperature range from about −80° to about +80° C., preferably between −30° and +50° C., in particular between −20° C. and room temperature.

The duration of the reaction depends on the reactants, the temperature and the solvent or solvent mixture and is normally between about ¼ and about 72 hours.

The reaction with acid halides can optionally be carried out in the presence of an acid-binding agent in order to bind the hydrogen halide released. Those which are suitable are in particular tertiary amines, such as, for example, triethylamine or dimethylaniline; inorganic bases, such as, for example, potassium carbonate or sodium carbonate; or alkylene oxides, such as, for example, propylene oxide. Even the presence of a catalyst, such as, for example, dimethylaminopyridine, may optionally be advantageous.

If the amino group is present in the compounds of the general formula (IV) in the form of a reactive derivative, it may be one of the type which is known from the literature for amidations. Thus, for example, silyl derivatives which are formed in the reaction of the compounds of the general formula (IV) with a silyl compound, such as, for example, trimethylchlorosilane or bis(trimethylsilyl)acetamide, are suitable. If the reaction is carried out using a compound of this type activated on the amino group, it is expedient to carry out the reaction in an inert solvent, such as, for example, methylene chloride, tetrahydrofuran or dimethylformamide.

Physiologically tolerable acid addition salts of the compounds of the general formula (I) which may be mentioned are, for example, those with hydrochloric acid, hydrobromic acid, nitric acid, phosphoric acid, sulfuric acid or organic acids, such as, for example, methanesulfonic acid, p-toluenesulfonic acid, p-ethylbenzenesulfonic acid or maleic acid.

The physiologically tolerable salts and acid addition salts can be obtained in a manner known per se by combining the compounds of the general formula (I) and the acid or base components in a suitable solvent, for example in aqueous-alcoholic solution.

The invention also relates to the intermediates of the general formula (VI)

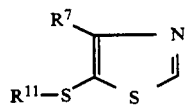 (VI)

in which $R^7$ has the meaning mentioned under formula II and $R^{11}$ stands for hydrogen, sodium or potassium.

5-Thiothiazoles of the general formula (VI)

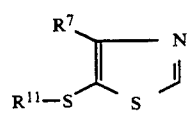 (VI)

in which $R^7$ has the above meaning, but cannot stand for hydrogen, and $R^{11}$ can be hydrogen, sodium or potassium, can be obtained by reacting compounds of the general formula (VII)

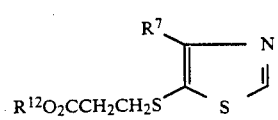 (VII)

in which $R^7$ has the above meaning—with the exception of hydrogen—and $R^{12}$ can be hydrogen or a $C_1$–$C_4$-alkyl radical, such as, for example, methyl, ethyl, propyl, iospropyl or butyl, preferably methyl and ethyl, but particularly ethyl, with bases at elevated temperature and isolating the corresponding mercaptide, for example, by precipitating with an organic solvent or by acidifying the free mercapto compound ($R^{11}$=H).

The products of the formula (VI) can be reacted with 7-ACS in a manner known per se after isolation or also directly without further purification to give the compounds of the general formula (III).

The reaction is preferably carried out in an organic solvent, preferably in methanol, ethanol or a mixture of water and one of the alcohols. When using alcohols as solvents, a solution of the corresponding sodium or potassium alcoholate in the same solvent is expediently used as the base. The reaction temperature is in general between 30° and 100° C., preferably between 60° and 80° C. The base component is added in amounts which are between approximately equimolar amounts and an excess of up to three-fold. The mercaptide can also be obtained, for example, by addition of sodium hydroxide solution to the aqueous-alcoholic solution.

The preparation of compounds of the general formula (VI), in which $R^7$ is equal to hydrogen, takes place from compounds of the general formula (VIII)

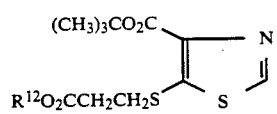 (VIII)

in which $R^{12}$ has the above meaning, by treatment with organic acids, such as, for example, trifluoroacetic acid or formic acid and decarboxylation of the resultant acid of the general formula (IX)

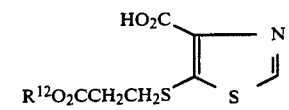 (IX)

in a customary manner, for example by heating, followed by a reaction with bases, according to the conditions described above, to give the desired heterocycle of the general formula (X)

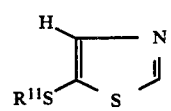 (X)

in which $R^{11}$ has the above meaning.

The preparation of the compounds of the general formula (VII) can be carried out in analogy to a process known from the literature, which is described in Liebigs Annalen, p. 2122–2125 (1986). Examples of compounds of the general formula (VII) are described in EP 0,194,572.

The compounds of the general formula (I) obtained according to the invention and their physiologically tolerable salts and acid addition salts show remarkably good antibacterial activity both against Gram-positive and Gram-negative bacterial microorganisms.

The compounds of the formula I are also unexpectedly highly active against penicillinase-forming and cephalosporinase-forming bacteria. Since they in addition show favorable toxicological and pharmacological properties, they represent useful chemotherapeutics.

The invention thus also relates to pharmaceutical preparations for the treatment of microbial infections, which comprise one or more of the compounds according to the invention.

The compounds of the general formula (I) and their physiologically tolerable salts and acid addition salts can be administered orally, intramuscularly or intravenously. Pharmaceutical preparations which contain one or more compounds of the general formula I as the active compound can be prepared by mixing the compounds of the formula (I) with one or more pharmacologically tolerable excipients or diluents, such as, for example, fillers, emulsifiers, lubricants, flavor enhancers, colorants or buffer substances, and bringing into a suitable galenical form of preparation, such as, for example, tablets, coated tablets, capsules or a suspension or solution suitable for parenteral administration.

Excipients or diluents which may be mentioned are, for example, tragacanth, lactose, talc, agar agar, polyglycols, ethanol and water. Buffer substances are, for example, organic compounds such as, for example, N,N'-dibenzylethylenediamine, diethanolamine, ethylenediamine, N-methylglucamine, N-benzylphenethylamine, diethylamine, tris(hydroxymethyl)aminoethane or inorganic compounds, such as, for example, phosphate buffer, sodium bicarbonate or sodium carbonate. For parenteral administration, suspensions or solutions in water with or without buffer substances are preferred. It is also possible to administer the active compounds as such without excipients or diluents in a suitable form, for example in capsules.

Suitable doses of the compounds of the general formula I or their physiologically tolerable salts or acid addition salts are about 0.4 to 10 g/day, preferably 0.5 to 4 g/day, for an adult of about 80 kg body weight.

Individual or, in general, multiple doses can be administered, where the individual dose can contain the active compound in an amount of about 50 to 1000 mg, preferably of about 100 to 500 mg.

The following exemplary embodiments for syn compounds which can be prepared according to the invention are used to illustrate the invention further, but they do not limit it thereto.

PREPARATION OF STARTING SUBSTANCES

Preparation Example 1

Methyl 5-[(2-(methoxycarbonyl)ethylthio]thiazole)-4-carboxylate

A solution of 7.9 g (80 mmol) of methyl isocyanoacetate in 60 ml of anhydrous tetrahydrofuran was added dropwise at −40° C. to a suspension of 10 g (88 mmol) of potassium tert.-butylate in 80 ml of anhydrous tetrahydrofuran. The mixture was then cooled to −60° C. and a solution of 4.8 ml (80 mmol) of carbon disulfide in 60 ml of anhydrous tetrahydrofuran was added dropwise, the temperature being kept below −50° C. After completion of the addition, the batch was slowly allowed to come to 10° C. and 13.4 g (80 mmol) of methyl 3-bromopropionate were added and the mixture was stirred at room temperature for 2 h. After stripping off the solvent, the crude product was taken up in methylene chloride, washed with water, dried (MgSO$_4$) and concentrated. After recrystallization from ethyl acetate/cyclohexane (1+1), 13.8 g (66%) of the title compound were obtained.

M.p.: 74°–75° C. $^1$H-NMR (60 MHz, DMSO-d$_6$): δ (ppm)=2.8–3.3 (4H, m, 2×CH$_2$), 3.6 and 3.8 (6H, s, 2×OCH$_3$), 9.1 (1H, s, CH).

The following compounds were prepared analogously to Preparation Example 1:

Example 2

5-[(2-(Methoxycarbonyl)ethylthio]thiazole-4-carboxamide:

Yield: 46%; M.p.: 151°–152° C. (dioxane). $^1$H-NMR (60 MHz, DMSO): δ (ppm)=2.5–3.15 (4H, m, 2×CH$_2$), 3.66 (3H, s, OCH$_3$), 7.2–7.6 (2H, bs, NH$_2$), 8.6 (1H, s, CH)

Example 3

Tert-butyl 5-[(2-(methoxycarbonyl)ethylthio]-thiazole-4-carboxylate

Yield: 66%; M.p.: 62°–63° C. (Et$_2$O) $^1$H-NMR (60 MHz, DMSO): δ (ppm)=1.6 (9H, s, tert.butyl), 2.5–3.2 (4H, m, 2×CH$_2$), 3.66 (3H, s, OCH$_3$), 8.6 (1H, s, CH).

Example 4

N-Pyrrolidinyl-5-[(2-(methoxycarbonyl)ethylthio]-thiazole-4-carboxamide

Yield: 61%; M.p.: 78°–80° C. $^1$H-NMR (60 MHz, DMSO): δ (ppm)=1.7–2.1 (8H, m, pyrrolidinyl-CH$_2$), 2.6–3.3 (4H, m, 2×CH$_2$), 3.65 (3H, s, OCH$_3$), 8.6 (1H, s, CH).

PREPARATION EXAMPLE 5

Methyl 5-mercaptothiazole-4-carboxylate 10.6 g (40 mmol) of the title compound from Preparation Example 1 were dissolved in 150 ml of methanol, 1.6 g (40 mmol) of sodium hydroxide was added and the mixture was heated under reflux for 1 h. After concentrating, the residue was taken up in ethyl acetate and adjusted to pH 2 with 2N hydrochloric acid. The organic phase was dried and concentrated. The crude product thus obtained was recrystallized from ethyl acetate/cyclohexane. 5 g (71%) of the title compound was obtained.

M.p.: 100° C. $^1$H-NMR (60 MHz, DMSO-d$_5$): δ (ppm)=3.65 (3H, s, OCH$_3$), 9.05 (1H, s, thiazole-H).

PREPARATION EXAMPLE 6

5-Mercaptothiazole-4-carboxylic acid 2.6 g (15 mmol) of the title compound from Preparation Example 5 were dissolved in a 1:1 mixture of water/methanol, 1.2 g (30 mmol) of sodium hydroxide were added and the mixture was kept at 80° C. for 3 h. The methanol was then removed by distillation, and the residue was acidified using 2N hydrochloric acid and extracted using methylene chloride. After drying (MgSO$_4$) and stripping off the solvent, the crude product obtained was recrystallized from acetone. 1.4 g (58%) of the desired title compound was obtained.

M.p.: 156°–157° C.

PREPARATION EXAMPLE 7

5-Mercaptothiazole-4-carboxamide sodium salt 8.9 g (36 mmol) of the title compound from Preparation Example 2 were suspended in 150 ml of methanol and added to a solution of 0.83 g (36 mmol) of sodium in 75 ml of methanol and the mixture was heated under reflux for 1 h. It was then concentrated, the residue was taken up in a little methanol, the solution was added dropwise to 0.5 l of diisopropyl ether and the product was filtered off with suction and dried ($CaCl_2$). 4.8 g (73%) of the desired title compound were obtained, which was further processed without additional purification.

PREPARATION EXAMPLE 8

N-Pyrrolidino-5-mercaptothiazole-4-carboxamide sodium salt 15 g (50 mmol) of the title compound from Preparation Example 4 were dissolved in a sodium methylate solution which was prepared from 1.3 g (55 mmol) of sodium and 200 ml of methanol, and the mixture was heated under reflux for 40 minutes. It was then concentrated and the crude product was further processed without additional purification.

PREPARATION EXAMPLE 9

5-Mercaptothiazole sodium salt

Step 1

5-[2-Methoxycarbonyl)ethylthio]thiazole-4-carboxylic acid 7.8 g (26 mmol) of the title compound from Preparation Example 3 were stirred in 100 ml of trifluoroacetic acid for 30 minutes. The mixture was then concentrated, the residue was taken up in methylene chloride and concentration again on a rotary evaporator, and ethyl acetate was added to the crystal magma obtained. After stirring briefly, the crystals were filtered off with suction and washed with a mixture of ether/petroleum ether (1:1). 6.2 g (97%) of the desired title compound were obtained.

M.p.: 112°–114° C. $^1$H-NMR (60 MHz, DMSO-$D_6$): δ (ppm)=2.5–3.2 (4H, m, 2×$CH_2$), 3.66 (3H, s, $OCH_3$), 9.0 (1H, s, CH).

Step 2

5-[2-(Methoxycarbonyl)ethylthio]thiazole 6.1 g (25 mmol) of step 1 was heated to 180° C. without solvent until the evolution of gas, which sets in gradually, is complete. After cooling, the solidified residue was taken up in a little ethyl acetate and chromatographed ($SiO_2$; acetone/cyclohexane=1+1). Subsequent bulb tube distillation (temperature 180° C., 0.1 mm Hg) yielded 2.8 g (56%) of the desired title compound.

$^1$H-NMR (60 MHz, DMSO-$d_6$): δ (ppm)=2.5–3.2 (4H, m, 2×$CH_2$), 3.66 (3H, s, $OCH_3$), 7.9 and 9.25 (2H, s, thiazole-H).

Step 3

5-Mercaptothiazole sodium salt 9 g (45 mmol) of 5-[2-(methoxycarbonyl)ethylthio]-thiazole (step 2) were dissolved in 90 ml of methanol and added dropwise to a solution of 1 g (45 mmol) of sodium in 180 ml of methanol and then kept under reflux for 1.5 h. After concentrating, the residue was taken up in a little methanol, the solution was added dropwise to 1 l of diethyl ether, and the precipitate was filtered off with suction and dried. 5.3 g (84%) of the desired title compound were obtained, which was further processed without additional purification.

$^1$H-NMR (60 MHz, DMSO-$d_6$): δ (ppm)=7.3 and 8.5 (2H, s, thiazole-H).

PREPARATION EXAMPLE 10

7-Amino-3-[(4-methoxycarbonyl-5-thiazolyl)thiomethyl]ceph-3-em-4-carboxylic acid 1.7 g (2 eq.) of sodium hydrogencarbonate were added to a suspension of 2.7 g (10 mmol) of 7-ACS in 20 ml of water and 1.7 g (10 mmol) of methyl 5mercaptothiazole-4carboxylate (Preparation Example 5) were added after dissolution. The solution was then kept at 65° C. for 5 h and extracted twice with ethyl acetate after cooling. The aqueous phase was then acidified to pH 3 and the precipitated product was filtered off with suction and dried. 2.6 g (68%) of the desired title compound were obtained.

M.p.: 290° C. (with decomposition); IR (KBr): 3420–2550, 1800, 1700, 1620, 1540, 1045 and 780 $cm^{-1}$. $^1$H-NMR (60 MHz, DMSO-$d_6$): δ (ppm)=3.6 (2H, d, S-$CH_2$), 3.66 (3H, s, $OCH_3$), 4.2 (2H, d, —$CH_2$SHet), 4.6–5.1 (2H, m, H-6 and H-7).

The following compounds were prepared analogously to Preparation Example 10:

PREPARATION EXAMPLE 11

7-Amino-3-[(4-carbamoyl-5-thiazolyl)thiomethyl]-ceph-3-em-4-carboxylic acid

M.p.: 202° C. (with decomposition); IR (KBr): 3500–2500, 1785, 1650, 1400, 1050 $cm^{-1}$. $^1$H-NMR (60 MHz, DMSO-$d_6$): δ (ppm)=3.6 (2H, d, S-$CH_2$), 4.15 (2H, d, —$CH_2$), 4.15 (2H, d, —$CH_2$S-Het), 4.6–5.1 (2H, m, H-6 and H-7), 7.5 (2H, broad s, $CONH_2$), 9.0 (1H, s, CH).

PREPARATION EXAMPLE 12

7-Amino-3-[(5-thiazole)-thiomethyl]ceph-3-em-4-carboxylic acid

M.p.: 229° C. (with decomposition); IR (KBr): 3500–2450, 1800, 1620, 1535, 1410, 1345, 800 $cm^{-1}$. $^1$H-NMR (60 MHz, DMSO-$d_6$): δ (ppm)=3.6 (2H, d, S-$CH_2$), 4.2 (2H, d, —$CH_2$S-Het), 4.6–5.1 (2H, m, H-6and H-7), 7.95 (1H, s, H-4 thiazole), 9.2 (1H, s, H-2thiazole).

PREPARATION EXAMPLE 13

7-Amino-3-[(4-pyrrolidinocarbonyl-5-thiazolyl)thiomethyl]ceph-3em-4-carboxylic acid IR (KBr): 1805, 1630, 1345, 1045, 795 $cm^{-1}$. $^1$H-NMR (60 MHz, DMSO-$d_6$): δ (ppm)=1.66–2.0 (8H, m, pyrrolidinocarbonyl), 3.6 (2H, d, S-$CH_2$), 4.1 (2H, d, $CH_2$SHet), 4.6–5.0 (2H, m, H-6and H-7), 9.2 (1H, s, thiazole H).

PREPARATION EXAMPLE 14

7-Amino-3-[(4-hydroxycarbonyl-5-thiazolyl)thiomethyl]ceph-3-em-4-carboxylic acid IR (KBr): 3500–2500, 1790, 1700, 1390 $cm^{-1}$. M.p.: 220° C. (with decomposition).

B) WORKING EXAMPLES

Example 1

7-[2-(2-Aminothiazol-4-yl)-2-(Z)-methoxyimino-acetamido]3-[4-methoxycarbonyl-1,3-thiazol-5-yl)thiomethyl]ceph-3-em-4-carboxylic acid

3.7 g (24 mmol) of N-hydroxybenzotriazole (HOBT) and 4.95 g (24 mmol) of dicyclohexylcarbodiimide were added successively to a solution of 4.4 g (22 mmol) of 2-aminothiazol-4-yl-2-(Z)-methoxyiminoacetic acid in 200 ml of DMF and the mixture was stirred at room temperature for 4 h. Resultant dicyclohexylurea was filtered off with suction and 7.75 g (20 mmol) of 7-amino-3-[(4-methoxycarbonyl-1,3-thiazol-5-yl)thiomethyl]ceph-3-em-4-carboxylic acid (Preparation Example 10) were added and the mixture was stirred at room temperature for 10 h. The precipitate ped off in vacuo (0.1 mm Hg). The residue was taken up in 100 ml of water, covered with a layer of ethyl acetate and brought into solution by adding sodium hydrogencarbonate. The phases were then separated and the aqueous solution was adjusted to pH 3 using 2N hydrochloric acid. After 15 minutes stirring, the product was filtered off with suction and dried in vacuo (phosphorus pentoxide). 8.6 g (75%) of the desired title compound were obtained.

M.p.: 170° C. (with decomposition); IR (KBr): 1780, 1530, 1265, 1045 cm$^{-1}$ $^1$H-NMR (270 MHz, DMSO-d$_6$): δ (ppm)=3.57 and 3.75 (2H, AB, J=18 Hz, SCH$_2$), 3.83 and 3.85 (6H, 2xs, CO$_2$CH$_3$ and =N—OCH$_3$), 4.15 and 4.32 (2H, AB, J=12 Hz, 3'—CH$_2$), 5.15 (1H, d, J=6 Hz, 6-H), 5.78 (1H, dd, J=6 Hz, 7-H), 6.73 (1H, s, thiazole-H), 7.2 (2H, s, NH$_2$), 9.05 (1H, s, —S—CH=N), 9.62 (1H, d, NH).

WORKING EXAMPLE 2

7-[2-(2-Aminothiazol-4-yl)-2-(Z)-methoxyimino-acetamido]-3-[(4-carbamoyl-1,3-thiazol-5-yl)thiomethyl]ceph-3-em-4-carboxylic acid

Preparation was carried out analogously to Working Example 1.

M.p.: 191° C. (with decomposition); IR (KBr): 1775, 1660, 1045 cm$^{-1}$. $^1$H-NMR (270 MHz, DMSO-d$_6$): δ (ppm)=3.54 and 3.74 (2H, AB, J=18 Hz, SCH$_2$), 3.82 (3H, s, OCH$_3$), 4.17 and 4.3 (2H, AB, J=12 Hz, 3'—CH$_2$), 5.15 (1H, d, J=6.5 Hz, 6-H), 5.77 (1H, dd, J=6.5 Hz, 7-H), 6.75 (1H, s, thiazole-H), 7.2 (2H, s, NH$_2$ of thiazole), 9.05 (1H, s, S—CH=N—), 9.62 (1H, d, NH).

WORKING EXAMPLE 3

7-[2-(2-aminothiazol-4-yl)-2-(Z)-methoxyimino-acetamido]3-[(1,3-thiazol-5-yl)thiomethyl]ceph-3-em-4-carboxylic acid

Preparation was carried out analogously to Working Example 1.

IR (KBr): 1780, 1660, 1045 cm$^{-1}$. $^1$H-NMR (270 MHz, DMSO-d$_6$): δ (ppm)=3.5 and 3.72 (2H, AB, J=18 Hz, SCH$_2$), 3.83 (3H, s, OCH$_3$), 4.14 and 4.32 (2H, AB, J=12 Hz, 3'—CH$_2$), 5.15 (1H, d, J=6 Hz, 6-H), 5.77 (1H, dd, J=6 Hz, 7-H), 6.75 (1H, x, thiazole H), 7.2 (2H, s, NH$_2$), 8.05 (1H, s, 2-H of Het.), 9.21 (1H, s, 4-H of Het.), 9.6 (1H, d, NH).

WORKING EXAMPLE 4

7-[2-(2-Aminothiazol-4-yl)-2-(Z)-hydroxyimino-acetamido]3-[(4-methoxycarbonyl-1,3-thiazol-5-yl)thiomethyl]ceph-3-em-4-carboxylic acid

Step 1

7-[2-(2-Tritylaminothiazol-4-yl)-2-(Z)-trityl-oximino-acetamido]-3-[4-methoxycarbonyl-1,3-thiazol-5-yl)thiomethyl]ceph-3-em-4-carboxylic acid

0.28 mg of triethylamine were added dropwise to a solution of 1.0 g (1.5 mmol) of 2-(2-tritylaminothiazol-4-yl)-2-(Z)-trityl-oximino-acetic acid in 20 ml of anhydrous methylene chloride, the mixture was cooled to −20° C. and 0.31 g of phosphorus pentachloride (1.5 mmol) were then introduced. After 15 minutes at this temperature, the solvent was stripped off in vacuo and subsequently distilled using methylene chloride/acetone (1+1). The residue was then taken up in 14 ml of acetone and the solution was added dropwise at 0° C. to a solution of 0.58 g (1.5 mmol) of 7-amino-3-[(4-methoxycarbonyl-1,3-thiazol-5-yl)thiomethyl]ceph-3-em-4-carboxylic acid (Preparation Example 10) in 14 ml of acetone and 20 ml of water, to which 165 mg of sodium hydrogencarbonate and 0.56 ml of triethylamine had previously been added. After 30 minutes at 0° C. and stirring at room temperature for 1 h, the mixture was adjusted to pH 3 using 2N hydrochloric acid and extracted three times using 100 ml of ethyl acetate each time. The organic phase was dried (MgSO$_4$) and concentrated in vacuo. After chromatography (SiO$_2$; chloroform, cyclohexane, ethanol, glacial acetic acid=5+3+1+0.5), 250 mg of the desired title compound were obtained which were further processed in the next step.

Step 2

7-[2-(2-Aminothiazol-4-yl)-2-(Z)-hydroxyimino-acetamido]-3-[(4-methoxycarbonyl-1,3-thiazol-5-yl)thiomethyl]ceph3-em-4-carboxylic acid

250 mg of the compound obtained in step 1 were dissolved in 20 ml of 80% strength formic acid and stirred at room temperature for 90 minutes. Resultant triphenylcarbinol was then filtered off with suction and the filtrate was concentrated in vacuo. The residue was taken up in toluene a number of times and the solvent was stripped off in vacuo. The residue was then dissolved using 20 ml of dilute sodium hydrogencarbonate solution, the solution was acidified to pH 3 using 2N hydrochloric acid, and the precipitate was filtered off with suction and dried in vacuo (phosphorus pentoxide). 80 mg of the desired title compound were obtained.

M.p.: 112° C. (with decomposition); IR (KBr): 1770, 1535, 1260, 1045 cm$^{-1}$. $^1$H-NMR (270 MHz, DMSO-d$_6$): δ (ppm)=3.5 and 3.73 (2H, AB, J=18 Hz, SCH$_2$), 3.65 (3H, s, OCH$_3$), 4.0 and 4.28 (2H, AB, J=12 Hz, 3'—CH$_2$), 5.13 (1H, d, J=6 Hz, 6-H), 5.76 (1H, dd, J=6 Hz, 7-H), 6.68 (1H, s, aminothiazole H), 7.15 (2H, bs, NH$_2$), 7.6 (2H, s, amide NH$_2$), 9.45 (1H, d, J=18 Hz, NHCO), 11.3 (1H, bs, oxime-H).

WORKING EXAMPLE 5

7-[2-(2-Aminothiazol-4-yl)-2-(Z)-hydroxyimino-acetamido]-3-[(4-carbamoyl-1,3-thiazol-5-yl)thiomethyl]ceph-3-em-4-carboxylic acid

Step 1

7-[2-(tritylaminothiazol-4-yl)-2-(Z)-trityl-oximino-acetamido]-3-[4-carbamoyl-1,3-thiazol-5-yl)thiomethyl]-ceph-3-em-4-carboxylic acid 0.37 ml (1 eq.) of triethylamine was added dropwise to a solution of 1.88 g (2.8 mmol) of 2-(2-tritylaminothiazol-4-yl)-2-(Z)-trityl-oximino-acetic acid in 20 ml of anhydrous methylene chloride, the mixture was cooled to 20° C. and 0.56 g (2.8 mmol) of phosphorus pentachloride was then introduced. After 15 minutes at this temperature, the solvent was stripped off in vacuo and subsequently distilled using methylene chloride/acetone (1+1). The residue was then taken up in 14 ml of acetone and the solution was added dropwise at 0° C. to a solution of 0.75 g (2 mmol) of 7-amino-3-[(4-carbamoyl-1,3-thiazol-5-yl)thiomethyl]ceph-3-em-4-carboxylic acid (Preparation Example 11) in 14 ml of acetone and 20 ml of water, to which 220 mg of sodium hydrogencarbonate and 0.74 ml of triethylamine had previously been added. After 30 minutes at 0° C. and subsequently stirring at room temperature for 1 h, the mixture was adjusted to pH 3 using 2N hydrochloric acid and extracted three times using 75 ml of ethyl acetate each time. The organic phase was dried (MgSO$_4$) and concentrated in vacuo. After chromatography (SiO$_2$; chloroform, cyclohexane, ethanol, glacial acetic acid=5+3+1+0.5), 0.9 g of the desired title compound was obtained, which was further processed in the next step.

Step 2

7-[2-(2-Aminothiazol-4-yl)-2-(Z)-hydroxyimino-acetamido]-3-[(4-carbamoyl-1,3-thiazol-5-yl)thiomethyl]ceph-3-em-4-carboxylic acid 900 mg (0.87 mmol) of the compound obtained in step 1 were dissolved in 25 ml of 80% strength formic acid and the mixture was stirred at room temperature for 90 minutes. Resultant triphenylcarbinol was then filtered off with suction and the filtrate was concentrated in vacuo. The residue was then dissolved using 20 ml of dilute sodium hydrogencarbonate solution, and the solution was filtered and then acidified to pH 3 using 2N hydrochloric acid. The precipitate was then filtered off with suction and dried in vacuo (phosphorus pentoxide). 280 mg (59%) of the desired title compound were obtained.

M.p.: 118° C. (with decomposition) IR: 1780, 1540, 1265, 1045 cm$^{-1}$. $^1$H-NMR (270 MHz, DMSO-d$_5$): δ (ppm)=3.5 and 3.72 (2H, AB, J=18 Hz, SCH$_2$), 4.0 and 4.28 (2H, AB, J=12 Hz, 3'CH$_2$), 5.13 (1H, d, J=6 Hz, 6-H), 5.76 (1H, dd, J=6 Hz, 7-H), 6.66 (1H, s, aminothiazole H), 7.15 (2H, bs, NH$_2$), 7.6 (2H, s, amide-NH$_2$), 9.45 (1H, d, J=8 Hz, NHCO), 11.3 (1H, bs, oxime-H).

WORKING EXAMPLE 6

7-[2-(2-Aminothiazol-4-yl)-2-(Z)-carboxymethoxyimino-acetamido]-3-[(4-pyrrolidinocarbonyl-1,3-thiazol-5-yl)thiomethyl]ceph-3-em-4-carboxylic acid trifluoroacetate

Step 1

7-[2-(2-Aminothiazol-4-yl)-2-(Z)carboxy-tert-butylmethoxyimino-acetamido]-3-[(4-pyrrolidinocarbonyl-1,3-thiazol-5-yl)thiomethyl]ceph-3-em-4-carboxylic acid 300 mg (2 mmol) of N-hydroxybenzotriazole and 450 mg (2.2 mmol) of dicyclohexylcarbodiimide were added to a solution of 600 mg (2 mmol) of 2-aminothiazol-4-yl-2-(Z)-carboxy-tert-butyl-methoxyiminoacetic acid in 30 ml of dimethylformamide and the mixture was subsequently stirred for 30 minutes. 825 mg (2 mmol) of 7-amino-3-[(4-pyrrolidinocarbonyl-1,3-thiazol-5-yl)thiomethyl]ceph-3-em-4-carboxylic acid (Preparation Example 13) were then added and the mixture was stirred at room temperature for 8 h. Resultant dicyclohexylurea was then filtered off with suction and the solvent was removed in vacuo (0.1 mm Hg). The residue was then dissolved using 0.1N sodium hydrogencarbonate solution and the solution was extracted with ethyl acetate. The phases were then separated and the aqueous solution was adjusted to pH 3 using 2N hydrochloric acid. The product was filtered off with suction and further processed in the next step without additional purification.

M.p.: 180° C. (with decomposition),

Step 2

7-[2-(2-Aminothiazol-4-yl)-2-(Z)-carboxymethoxyiminoacetamido]-3-[(4-pyrrolidinocarbonyl-1,3-thiazol-5-yl)thiomethyl]ceph-3-em-4-carboxylic acid trifluoroacetate 400 mg (0.56 mmol) of step 1 were dissolved in 10 ml of trifluoroacetic acid and subsequently stirred for 30 minutes. The solvent was then stripped off and the residue was thoroughly stirred with diethyl ether. 363 mg of the desired title compound were thus obtained.

M.p.: 170° C. (with decomposition) IR (KBr): 1780, 1670, 1630, 1190, 1045 cm$^{-1}$. $^1$H-NMR (270 MHz, DMSO-d$_6$): δ (ppm)=1.83 (8 H, bs, pyrrolidinocarbonyl), 3.5 and 3.75 (2 H, AB, J=18 Hz, SCH$_2$), 3.95 and 4.2 (2H, AB, J=12 Hz, 3'—CH$_2$), 4.62 (2H, s, CH$_2$CO$_2$H), 5.16 (1H, d, J=6.5 Hz, 6-H), 5.77 (1H, dd, J=6.5×H$_2$, 6.75 (1 H, s, aminothiazole H), 9.12 (1H, s, thiazole-H of 3'-Het).

WORKING EXAMPLE 7

2,2-Dimethylpropionyloxymethyl 7-[2-(2-aminothiazol-4-yl)-2-(Z)-methoxyimino-acetamido]-3-[4-methoxycarbonyl-1,3-thiazol-5-yl)thiomethyl]ceph-3-am-4-carboxylate 0.6 g (2.8 mmol) of iodomethyl 2,2-dimethylpropanoate were added dropwise at 0° C. to a solution of 1.22 g (2 mmol) of 7-[2-(2-aminothiazol-4-yl)-2-(Z)-methoxyimino-acetamido]-3-[(4-methoxycarbonyl-1,3-thiazol-5-yl)thiomethyl]ceph-3-em-4-carboxylic acid potassium salt in 15 ml of anhydrous DMF and the mixture was subsequently stirred at this temperature for 2.5 h. It was then poured into 100 ml of 2% strength sodium hydrogencarbonate solution and extracted three times using 100 ml of ethyl acetate each time. The combined organic solutions were then washed with water and saturated sodium chloride solution, dried over $Na_2SO_4$ and concentrated. 0.7 g of an abovementioned product was obtained, which was triturated with diethyl ether. The solid product was filtered off with suction and dried over phosphorus pentoxide in vacuo. 300 mg of the desired title compound were obtained.

M.p.: 120° C. (with decomposition): IR (KBr): 1780, 1750, 1675, 1110 $cm^{-1}$. $^1H$-NMR (270 MHz, DMSO-$d_6$): δ (ppm)=1.15 (9H, s, tert.-butyl), 3.75 (2H, AB, J=18 Hz, $SCH_2$), 3.85 and 3.87 (6H, 2x s, $CO_2CH_3$ and=N-$OCH_3$), 4.2 (2H, AB, J=12 Hz, 3'—$CH_2$), 5.2 (1H, d, J=5 Hz, 6-H), 5.78 and 5.9 (3H, AB and g, J=5 Hz, —$CH_2OCO$ and 7-H), 6.75 (1H, s, thiazole-H), 7.25 (2H, bs, $NH_2$), 9.05 (1H, s, —S—CH=N), 9.65 (1H, d, J=8 Hz, NHCO).

WORKING EXAMPLE 8

7-[2-(2-Aminothiazol-4-yl)-2-(Z)-methoxyimino-acetamido]-3-[(4-carboxy-1,3-thiazol-5-yl)thiomethyl]-ceph-3-em-4-carboxylic acid.

The compound was prepared analogously to Working Example 1.

IR (KBr): 3500-2500, 1790, 1700, 1046 $cm^{-1}$. $^1H$-NMR (270 MHz, DMSO-$d_6$): δ (ppm)=3.56 and 3.75 (2H, AB, J=18 Hz, $SCH_2$), 3.83 (2H, S, =N-$OCH_3$), 4.15 and 4.31 (2H, AB, J=12 Hz, 3'—$CH_2$), 5.15 (1H, d, J=6 Hz, 6-H), 5.78 (1H, dd, J=6 Hz, 7-H), 6.71 (1H, s, thiazole-H), 7.2 (2H, s, $NH_2$), 9.05 (1H, s, —S—CH=N), 9.60 (1H, d, NH), 11.1 (1H, s, $CO_2H$),

We claim:

1. A cephalosporin derivative of the formula (I)

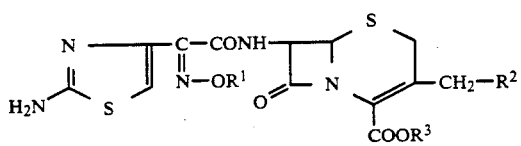

or a physiologically tolerable salt or acid addition salt thereof, in which $R^1$ denotes hydrogen, unsubstituted or substituted $C_1$-$C_6$-alkyl, unsubstituted or substituted $C_2$-$C_6$-alkenyl, $C_2$-$C_6$-alkynyl, $C_3$-$C_7$-cycloalkyl, $C_4$-$C_7$-cycloalkenyl, the group

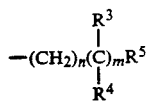

in which m or n in each case denotes 0 or 1, $R^3$ and $R^4$ are identical or different and denote hydrogen, aryl, a $C_1$-$C_4$-alkyl group or, together with the carbon atom to which they are bonded, form a methylene or a $C_3$-$C_7$-cycloalkylidene group; $R^5$ denotes a group —$CO_2R^6$ in which $R^6$ denotes hydrogen, $C_1$-$C_4$-alkyl or an equivalent of an alkali metal, alkaline earth metal or ammonium base or diisopropylamine, dicyclohexylamine or triethylamine; $R^2$ denotes a 5-thio-1,3-thiazole radical of the formula (II)

in which $R^7$ denotes hydrogen, carboxyl, $C_1$-$C_4$-alkoxycarbonyl or carbamoyl, in which the amino group is unsubstituted or is monosubstituted or disubstituted by $C_1$-$C_4$-alkyl or two of the alkyl groups on the nitrogen are closed to give a dimethylene to pentamethylene ring and $R^3$ denotes hydrogen, a physiologically tolerable cation or an easily cleavable ester group and in which the $R^1O$ group is in the syn position.

2. 7-[2-(2-Aminothiazol-4-yl)-2-(Z)-methoxyiminoacetamido]-3-[4-methoxycarbonyl-1,3-thiazol-5-yl)-thiomethyl]ceph-3-em-4-carboxylic acid.

3. 7-[2-(2-Aminothiazol-4-yl)-2-(Z)-methoxyiminoacetamido]-3-[(4-carbamoyl-1,3-thiazol-5-yl)-thiomethyl]ceph-3-em-4-carboxylic acid.

4. 7-[2-(2-Aminothiazol-4-yl)-2-(Z)-methoxyiminoacetamido]-3-[(1,3-thiazol-5-yl)thiomethyl]ceph-3-em-4-carboxylic acid.

5. 7-[2-(2-Aminothiazol-4-yl)-2-(Z)-hydroxyiminoacetamido]-3-[(4-methoxycarbonyl-1,3-thiazol-5-yl)thiomethyl]ceph-3-em-4-carboxylic acid.

6. 7-[2-(2-Aminothiazol-4-yl)-2-(Z)-hydroxyiminoacetamido]-3-[(4-carbamoyl-1,3-thiazol-5-yl)-thiomethyl]ceph-3-em-4-carboxylic acid.

7. A cephalosporin derivative of the formula (I) as claimed in claim 1, in which $R^1$ is $C_1$-$C_4$-alkyl which is unsubstituted or is monosubstituted or polysubstituted by halogen, $C_1$-$C_6$-alkylthio, $C_1$-$C_6$-alkyloxy, phenyl, pyridyl, furyl, unsubstituted $C_2$-$C_6$-alkenyl or $C_2$-$C_6$-alkenyl which is monosubstituted or polysubstituted by halogen.

8. A pharmaceutical composition having antibacterial action comprising a pharmaceutically effective amount of a compound of the formula (I) as claimed in claim 1 together with a pharmaceutically acceptable carrier.

9. A method for the production of a pharmaceutical composition having antibacterial action which comprises incorporating in said composition a compound of the formula (I) as claimed in claim 1.

10. A method for the treatment of microbial infections which comprises administering to a host in need of such treatment a pharmaceutical composition as claimed in claim 8.

11. A method for the treatment of microbial infections which comprises administering to a host in need of such treatment a pharmaceutically effective amount of a compound of the formula (I) as claimed in claim 1.

* * * * *